(12) United States Patent
Tjosas

(10) Patent No.: US 8,835,690 B2
(45) Date of Patent: Sep. 16, 2014

(54) PROCESS FOR THE PRODUCTION OF AMINO ALCOHOLS

(75) Inventor: Freddy Tjosas, Sarpsborg (NO)

(73) Assignee: Borregaard AS, Sarpsborg (NO)

( * ) Notice: Subject to any disclaimer, the term of this patent is extended or adjusted under 35 U.S.C. 154(b) by 0 days.

(21) Appl. No.: 13/984,500

(22) PCT Filed: Feb. 9, 2012

(86) PCT No.: PCT/NO2012/050019
§ 371 (c)(1),
(2), (4) Date: Sep. 4, 2013

(87) PCT Pub. No.: WO2012/108777
PCT Pub. Date: Aug. 16, 2012

(65) Prior Publication Data
US 2013/0338401 A1    Dec. 19, 2013

(30) Foreign Application Priority Data
Feb. 10, 2011   (NO) .................................. 20110238

(51) Int. Cl.
*C07C 213/04* (2006.01)
*C07C 213/02* (2006.01)
*B01J 19/00* (2006.01)

(52) U.S. Cl.
CPC ........... *C07C 213/04* (2013.01); *B01J 19/0093* (2013.01); *B01J 2219/00792* (2013.01)
USPC .......................................... 564/478; 564/475

(58) Field of Classification Search
CPC ........................ C07C 213/02; C07C 213/04
USPC .................................. 564/475, 478, 479, 480
See application file for complete search history.

(56) References Cited

U.S. PATENT DOCUMENTS

| | | | | | |
|---|---|---|---|---|---|
| 4,356,323 | A | * | 10/1982 | Kleemann et al. | 564/475 |
| 4,358,615 | A | * | 11/1982 | Kleemann et al. | 564/475 |
| 4,360,697 | A | * | 11/1982 | Kleemann et al. | 564/475 |
| 2012/0277471 | A1 | * | 11/2012 | Zhang et al. | 564/507 |

FOREIGN PATENT DOCUMENTS

CN   101250115 A   8/2008

OTHER PUBLICATIONS

Rider, T.H. et al. 1930 "Studies of Glycidol. II. Reactions with Secondary Amines," *Journal of the American Chemical Society* 52: 1528-1530, (1930).

* cited by examiner

*Primary Examiner* — Brian J Davis
(74) *Attorney, Agent, or Firm* — Knobbe, Martens, Olson & Bear, LLP

(57) ABSTRACT

The present invention relates to a process for the manufacture of APD and N-alkyl-APD wherein 1-CPD is reacted with aqueous ammonium or aqueous alkyl-amine under alkaline conditions and where the process is conducted in a continuous manner in a reactor comprising a tubular reactor wherein at least two reaction zones are established.

16 Claims, No Drawings

PROCESS FOR THE PRODUCTION OF AMINO ALCOHOLS

The present invention relates to a process for the production of alpha amino alcohols from the corresponding chlorinated alcohols as the starting material, and in particular the production of APD and N-alkyl-APD compounds from 1-CPD. The process is performed in a continuous reaction mode in a tubular reactor, where the reactor holds at least two reaction zones wherein the reaction conditions are individually varied and adapted. Performing the reaction by utilizing miniaturized apparatus known as microreactor or millireactor technology is additionally beneficial.

BACKGROUND OF THE INVENTION

Alpha-amino alcohols find wide use in industry, e.g. as starting materials and intermediates in the production of tensides, pestisides and as additives, e.g. to printing ink. 3-aminopropane-1,2-diol or 1-aminopropane-2,3-diol, also known as iso-serinol, hereinafter denoted APD, and N-methyl-3-aminopropane-1,2-diol, hereinafter denoted MAPD, as well as higher N-alkyl-APD compounds, are well known chemical compounds that are useful in medicine and also as a starting materials or as intermediates in the preparation of several useful end products.

Examples of the use of APD and MAPD are as intermediates in the production of medical products. In particular, APD and MAPD are used in the production of triiodinated aryl X-ray contrast agents. Examples of such compounds are those sold under the trademarks Omnipaque, Imagopaque, Visipaque, Ultravist, Xenetix, and Oxilan.

For the use in medicine in particular, it is important to obtain end products in the form of Active Pharmaceutical Ingredients (API) with high purity, as required according to e.g. the US Pharmacopeia. The purity requirements are particularly important for X-ray contrast agents which are injected in large doses, up to 150 g in one single dose. In the preparation of the end products, it is therefore of crucial importance that also the intermediates used, such as APD and MAPD, are of high purity to avoid laborious and expensive purification procedures as much as possible. In order to be able to provide APD and MAPD with acceptable purity and to a competitive price, it is always important to strive to optimize the processes of manufacture to convert as much as possible of the starting material to the desired end product, and to avoid as much as possible the formation of side products, and in particular such products that are difficult or laborious to remove from the desired end product.

In the production of chemicals, it is further of great importance to endeavor to use processes and starting materials that are as efficient, cheap and safe as possible, in order to avoid exposure of the workers and the environment of potential hazards.

APD and N-alkyl-APD are frequently produced from 1-chloro-2,3-propanediol, hereinafter 1-CPD, by reaction with aqueous ammonia or alkylamine, see e.g. Rider, T. H. and Hill, A. J., Studies of Glycidol. II. Reactions with secondary amines, JACS, 1930, 52, 1528-1530, EP 0470004 B1 (Daicel) and U.S. Pat. No. 6,111,142 (Dibra S.p.a.) The reaction is known to be a two-step reaction. The first step is the formation of oxiranylmethanol (hereinafter denoted by its trivial name glycidol) from 1-CPD under alkaline conditions. The second step comprises an aminolysis reaction wherein the glycidol formed in the first step is reacted with ammonia ammonium, or with a solution of an alkylamine, preferably in aqueous solution.

Traditionally, the process is conducted in batch reactors with continuous vigorous stirring, usually in a one pot fashion. The overall reaction is slow and a number of impurities are formed, such as glycerol, serinol, bis- and tert. hydroxyalkyl amines and di-ethers. For use as intermediates, e.g. in pharmaceuticals, the APD or N-alkyl-APD must be further purified to an acceptable level of purity, see e.g. U.S. Pat. No. 6,111,142.

CN patent application no. 1012501 15 of Zhejiang University describes the production of APD from a premix of 1-CPD and excess ammonia in a tubular reactor heated to a constant temperature of 60 to 100° C.

Alternatively, APD and N-alkyl-APD could be produced directly from glycidol. Processes for the production of alpha amino alcohols, and in particular of APD and N-alkyl-APD, from glycidol and its derivatives by reaction with aqueous ammonia or alkylamines, are described in the prior art, see for example U.S. Pat. No. 4,360,697 and U.S. Pat. No. 4,358,615 (both of Degussa AG), EP 0364708 (Kali Chemie) and EP 0470004 (Daicel), and references listed therein.

However, at ambient temperature, glycidol of high purity is a slightly viscous liquid that is unstable and is not often encountered in pure form. The compound is an irritant of the skin, eyes, and mucous membranes and is toxic by inhalation. 1-CPD is also known to be toxic by inhalation and if swallowed, and is irritating to skin, eyes, mucous membranes.

Therefore, since glycidol in the sufficiently pure form which is required, in particular in the preparation of intermediates for API manufacture, is unstable, and both glycidol and 1-CPD are toxic, there remains a desire to reach to processes and production methods wherein the safety is improved, preferably without increasing the manufacturing costs considerably.

SUMMARY OF THE INVENTION

In one aspect of the present invention, it is realized that the shortcomings in the state of art processes can be overcome by preparing APD and N-alkyl-APD by the reaction of 1-CPD with ammonia or alkyl amine under alkaline conditions in a continuous process mode. The continuous reaction should be performed in a reactor where the exposure of the reactants and intermediates (such as glycidol) to the environment is avoided as much as possible, and where the reaction conditions can be carefully monitored and controlled. The reactor should comprise a tubular reactor wherein at least two reaction zones are established, allowing for individual regulation of the process conditions. Preferably, the reactor is selected from nano-, micro- and millireactors which are themselves well known from the state of art.

DETAILED DESCRIPTION OF THE INVENTION

The continuous process for the manufacture of APD or N-alkyl-APD is initiated by continuous administering 1-CPD and an aqueous solution of a base into a tubular reactor. The reactor has at least two zones where reaction conditions, such as temperature, flow rates, pressure etc, can be varied. With tubular reactor is meant a reactor comprising an elongated reaction chamber, which is tubular and must be sufficiently long. The cross-section of the tube may vary both in size and geometry. The cross-section may be rectangular, oval or circular, or may be irregular e.g. by combining rectangular and circular geometries. All such cross-sections are comprised by the denomination "tubular cross-section". The elongated tubular reaction chamber may be straight or curved. Openings, such as inlets for the administration of reactants and/or outlets for sample collections should be available, at least at one point in each of the at least two segments of the reactor, preferable at three or more places along the elongated body of the reactor. Reactors known as microreactors or nanoreactors (hereinafter together denoted microreactor(s)) are particularly preferred. Such reactors are well known from the state of art, see for example Roberge, D. M., "Microreactor Technology: A Revolution for the fine Chemical and Pharmaceutical Industries?" Chem. Eng. Technol. 2005, 28, no 3, p. 318-322. Suitable microreactors are also commercially available, e.g. from Alfa-Laval AB.

By N-alkyl-APD is meant the compound APD being N-alkylated with a lower alkyl group, i.e. an alkyl group with 1 to 5 carbon atoms. The alkyl chain may be straight or branched. Within the definition of alkyl-APD is MAPD.

The first step of the reaction is the formation of glycidol:

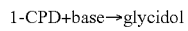

1-CPD+base→glycidol and is run under alkaline conditions.

Due to the toxicity of 1-CPD and glycidol, the reaction should be run in a closed reaction apparatus. It is therefore preferred not to premix the 1-CPD with the base prior to the administration to the reactor. It is, however, important that the 1-CPD and the base are thoroughly mixed in order to initiate the reaction of 1-CPD to form glycidol. The 1-CPD and the base are therefore administrated e.g. by injection into the tubular reactor with sufficient speed and through separate injection sites, in order to achieve a quick and thorough mixing of the reactants. Preferably, the injection sites are tubes joined together e.g. in a T- or Y-shaped manner, where turbulence is created in the area where the tubes are connected. Alternatively or additionally, thorough mixing of the reactants can also be secured by fitting a micromixer in a position at, or in the close vicinity of, the place where the tubes for administration of the reactants are connected to each other. By injection is meant any form of administration, including pumping the reactants into the reactor, e.g. by peristaltic pumps. The pumps should preferably be powerful enough to create turbulent flow at the mixing site of the injected fluids.

The formation of glycidol is favored by a temperature above ambient temperature, preferably a temperature from ambient temperature to about 60° C., more preferably from ambient temperature to about 50° C., and even more preferred from about 45 to about 35° C. Most preferably, this first segment of the tubular reactor forming the first reaction zone, is heated to allow for a reaction temperature from about 35° C. to about 45° C., in particular about 40° C.

The base should preferably be a strong base such as NaOH, KOH and Ca(OH)$_2$.

The molar amount of 1-CPD to base should be from about 1.2 to about 0.8 mole/mole, preferably from about 1.1 to about 0.9, more preferred from 1.0 to 0.9, in particular about 0.95.

The pH of the mixture should be kept between 10 and 13, preferably from pH 10 to 12, more preferred about pH 11 to provide favorable conditions for the formation of glycidol. Should the pH drop significantly, additional base may be added, e.g. at an additional inlet downstream the tubular reactor.

The reactants will run through the tubular reactor, e.g. under influence of gravity. If desired, a pumping device can be fitted into the tubular reactor to control the speed, e.g. to accelerate the flow of the reactants though the reactor channel. Additionally, the speed can be controlled by varying the shape of the tubes of the reactor, e.g. by making the reactor channels broader or narrower, or by including bends on the tubes. In this way, the continued mixing of the reactants and the product formed is ensured.

By carefully controlling the reaction conditions, the conversion of the 1-CPD to form glycidol will run at a desired and acceptable rate. When the reaction has run for a pre-desired time or when a desired conversion of the 1-CPD to glycidol is achieved, the second step of the process is initiated by administering ammonia or alkylamine into the reaction tube downstream in the reactor. At the initiation of the second step, the concentration of the 1-CPD at the site where the ammonia or alkylamine is administered should be less than 25 weight % of the concentration of the 1-CPD at the initiation of the process. Preferably less than 20 weight % or less than 15 weight % of the initial concentration of the 1-CPD should remain. Most preferred about 10 weight % or less should remain.

In the second step, ammonia or alkyl-amine, i.e. $C_1$-$C_5$ alkyl-amine, is added and will react with the glycidol formed in situ resulting in the formation of APD or N—$C_1$-$C_5$ alkyl-APD.

At the initiation of the second step, the temperature of the reaction mixture should be lowered to less than 20° C., preferably to less than 15° C., and particularly preferred to a temperature of about minus 2 to about 2° C. This can be done by exposing the reactor channels to a cooling medium. In the nucleophilic ring opening of the glycidol, temperature control is a key factor which determines the selectivity for the formation of APD or N-alkyl-APD, and for the unwanted formation of side products such as dimers and secondary amines, in particular serinol (2-amino-1,3-propanediol).

This second reaction step is run in the second reaction segment of the reactor forming the second reaction zone, where the reaction conditions are different from those of the first reactor zone. In this second reaction step, the formed glycidol is converted to APD or to N-Ci-C5-alkyl-APD by reaction with ammonia or $C_1$-$C_5$-alkyl-amine.

The ammonia or $C_1$-$C_5$-alkyl-amine should be added in excess to ensure a high conversion of glycidol to APD or alkyl-APD.

APD is a good nucleophile, even better than ammonia, and the formed APD may react with available glycidol to form unwanted secondary amines. Hence, a considerable excess of ammonia should be added to suppress the formation of secondary amines. With a considerable excess is meant a molar amount of not less than 2 moles per mole of the 1-CPD being administered, preferably at least 10 moles excess of ammonia, more preferred at least 15 moles, and even more preferred from 16 to 20 moles excess ammonia. The reaction should be run under alkaline conditions, preferably at a pH of not less than 10. If needed, additional amounts of alkali such as NaOH, KOH or Ca(OH)$_2$ may be added together with the ammonia or separately, and preferably before the addition of the ammonia. Alternatively, the pH may also be adjusted after the addition of ammonia to reach to the desired pH value.

In the reaction of forming MAPD by the reaction of the intermediate glycidol with monomethyl amine (MMA), it is observed that this reaction is faster than in the formation of APD. Less side products are formed, and the amount of alkali added and hence the pH at which the reaction is run is less critical. It is however preferred that the reaction should be run at a pH of not less that 10.

The ammonia and the alkyl amine are preferably administered as aqueous solutions. The concentration of the solution is not critical, however, concentrated solutions are preferred. The second reaction is run for the period of time necessary to obtain an optimal formation of the desired end products, APD or N—$C_1$-$C_5$-alkyl-APD, and with minimal formation of undesired side products such as dimers and secondary amines. The second step of the present reaction is preferably run in the same tubular reactor as in the first step. As noted above, the reaction component moves through the reactor under the influence of gravity, or if needed or desirable, under enhanced pressure.

At the outlet of the reactor, the reaction fluids containing the amine products are continuously collected in a vessel. The vessel may be of any kind including tubes, and may have temperature control and/or be protected from environmental influence.

The produced APD and N—$C_1$-$C_5$-alkyl-APD will be further processed to isolate and if necessary to further purify the final products with the desired purity by method known from the state of art, see e.g. U.S. Pat. No. 6,111,142, EP patent 0470004 and CN patent application 101250115.

EXPERIMENTAL

%, w % and w/w % means weight % unless stated otherwise.

Description of the Microreator

A microreactor consisting of ten chambers of 13.559 ml volume each, wherein the chambers were connected with U-bends of 0.4 ml each was used in the experiments. The total reactor volume is 139.19 ml. A commercial available reactor ART®PR37 from Alfa Laval AB was used in the Examples.

1-CPD and NaOH were injected separately through two inlets in the first chamber. Ammonia or methyl-amine was injected through a third inlet inlet in the fourth chamber.

The microreactor was divided into two different temperature zones. The first and second chambers were connected to a heating system and served as the heated part of the reactor. The fourth to tenth chambers were connected to a cooling system. In addition a Teflon tubing (i.d. 2.52 mm, 283 m) was added after the tenth and last chamber serving as a collection part and also providing additional residence time. The third chamber served as an insulating layer between the hot and cold zone.

Example 1

Synthesis of APD

The microreactor described above was used for the synthesis.

The reagents were injected at flow rates of:
1-CPD (conc. 99% in water, 3.0 ml/min),
NaOH (conc. 10%, 11.6 ml/min) and
$NH_3$ (conc. 25%, 56.4 ml/min).

This gave a residence time of 2.87 minutes for the glycidol formation in the first and second chambers, and 21.1 minutes for the aminolysis in the fourth to tenth chambers, giving a total residence time of 23.98 minutes. The temperature was held at about 42° C. in the first and second chambers, and about 18° C. in the fourth to tenth chambers. In the Teflon tubing collection part the temperature was about 22° C. (ambient temperature). Samples were collected after 50 minutes from the starting point. The yield was 67.4 area % APD based on the amount of 1-CPD used.

Example 2

Synthesis of MAPD

The microreactor described above was used for the synthesis.

The reagents were injected at flow rates of:
1-CPD (conc. 99% in water, 5.0 ml/min),
NaOH (conc. 10%, 19.4 ml/min) and
ethylamine (conc. 40%, 79.1 ml/min).

This gave a residence time of 1.72 minutes for the glycidol formation in the first and second chambers, and 14.5 minutes for the aminolysis in the fourth to tenth chambers, giving a total residence time of 16.21 minutes. The temperature was held at about 42° C. in the first and second chambers, and about 17° C. in the fourth to tenth chambers. In the Teflon tubing collection part the temperature was about 22° C. (ambient temperature). Samples were collected after 35 minutes from the starting point. The yield was 82.4 area % MAPD based on the amount of 1-CPD used.

The invention claimed is:

1. Process for the manufacture of APD and N—$C_1$-$C_5$-alkyl-APD comprising reacting 1-CPD with aqueous ammonia or aqueous $C_1$-$C_5$-alkyl-amine under alkaline conditions, wherein the process is conducted in a continuous manner in a reactor comprising a tubular reactor, and wherein at least two reaction zones are established.

2. Process of claim 1 wherein the tubular reactor is a microreactor or a millireactor.

3. Process of claim 1, wherein the reactor contains two separate reaction zones.

4. Process of claim 1, wherein glycidol is formed by the reaction of 1-CPD in alkaline conditions in a first reaction zone of the tubular reactor.

5. Process of claim 4, wherein at reactor inlets of the first reaction zone, 1-CPD and base are injected through separate inlets into a mixing zone at injection speeds sufficient to ensure thorough mixing of the reactants.

6. Process of claim 4, wherein alkali is added to keep the pH of the mixture between 10 and 13.

7. Process of claim 4, wherein the temperature in the first reaction zone of the tubular reactor is above ambient temperature.

8. Process of claim 7, wherein the temperature in the first reaction zone of the tubular reactor is up to about 60° C.

9. Process of claim 7, wherein the temperature in the first reaction zone of the tubular reactor is from about 35° C. to about 45° C.

10. Process of claim 1, wherein APD or N—$C_1$-$C_5$-alkyl-APD is formed by the reaction of glycidol with ammonia or with C1-C5-alkyl-amine in a second reaction zone of the tubular reactor.

11. Process of claim 10 wherein at least 2 moles of ammonia or $C_1$-$C_5$-alkylamine are added per mole of 1-CPD.

12. Process of claim 10, wherein the pH is not less than 10.

13. Process of claim 10, wherein the temperature in the second reaction zone of the tubular reactor is less than 20° C.

14. Process of claim 13, wherein the temperature in the second reaction zone of the tubular reactor is less than 15° C.

15. Process of claim 13, wherein the temperature in the second reaction zone of tubular reactor is from about −2° C. to about 2° C.

16. The process of claim 6, wherein the alkali is in the form of strong base.

* * * * *